(12) United States Patent
Lancaster

(10) Patent No.: US 9,969,968 B2
(45) Date of Patent: May 15, 2018

(54) HYDRODYNAMIC SEPARATION (HDS) FOR REMOVING PROTIST PREDATORS FROM ALGAL CROPS

(71) Applicant: Palo Alto Research Center Incorporated, Palo Alto, CA (US)

(72) Inventor: Cory Lancaster, South San Francisco, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 7 days.

(21) Appl. No.: 15/219,534

(22) Filed: Jul. 26, 2016

(65) Prior Publication Data

US 2018/0030401 A1 Feb. 1, 2018

(51) Int. Cl.
 C12N 1/12 (2006.01)
 C12M 1/00 (2006.01)
 C12M 1/36 (2006.01)
 C12Q 3/00 (2006.01)

(52) U.S. Cl.
 CPC ............ *C12N 1/12* (2013.01); *C12M 41/48* (2013.01); *C12M 47/02* (2013.01); *C12Q 3/00* (2013.01)

(58) Field of Classification Search
 CPC ............ B01D 21/265; B01D 2313/21; B01D 2313/38; B01D 61/18; B01D 63/08; B01D 63/088; B01D 71/10; B01D 71/68; B01D 21/0003; B01D 21/0087; B01D 21/34; B01D 2311/04; B01D 2311/2642; B01D 2311/2649; B01D 2311/266; C02F 1/76; C02F 2203/006; C02F 2209/005; C02F 2209/02; C02F 2209/03; C02F 2209/09; C02F 2209/40; C02F 3/006; C02F 3/12; C12M 41/48; C12M 47/02; C12N 1/12; C12Q 3/00; Y02W 10/15
 See application file for complete search history.

(56) References Cited

U.S. PATENT DOCUMENTS

| | | | |
|---|---|---|---|
| 7,534,336 B2 | 5/2009 | Voikel et al. |
| 8,268,169 B2 | 9/2012 | Lean et al. |
| 8,276,760 B2 | 10/2012 | Lean et al. |
| 8,404,093 B2 | 3/2013 | Volkel et al. |
| 8,518,235 B2 | 8/2013 | Volkel et al. |
| 8,647,479 B2 | 2/2014 | Lean et al. |
| 8,852,446 B2 | 10/2014 | Lean et al. |
| 8,869,987 B2 | 10/2014 | Lean et al. |
| 8,875,903 B2 | 11/2014 | Lean et al. |
| 8,931,644 B2 | 1/2015 | Lean et al. |
| 2005/0247564 A1 | 11/2005 | Volkel et al. |
| 2008/0128331 A1 | 6/2008 | Lean et al. |
| 2008/0230458 A1 | 9/2008 | Lean et al. |
| 2009/0050538 A1 | 2/2009 | Lean et al. |
| 2009/0114601 A1 | 5/2009 | Lean et al. |
| 2009/0114607 A1 | 5/2009 | Lean et al. |
| 2009/0283452 A1 | 11/2009 | Lean et al. |
| 2009/0283455 A1 | 11/2009 | Lean et al. |
| 2010/0072142 A1 | 3/2010 | Lean et al. |
| 2010/0140092 A1 | 6/2010 | Volkel et al. |
| 2010/0314263 A1 | 12/2010 | Lean et al. |
| 2010/0314323 A1 | 12/2010 | Lean et al. |
| 2010/0314325 A1 | 12/2010 | Lean et al. |
| 2010/0314327 A1 | 12/2010 | Lean et al. |
| 2011/0108491 A1 | 5/2011 | Lean et al. |
| 2012/0074074 A1 | 3/2012 | Lean et al. |
| 2012/0145546 A1 | 6/2012 | Volkel et al. |
| 2012/0145647 A1 | 6/2012 | Volkel et al. |
| 2012/0152814 A1 | 6/2012 | Lean et al. |
| 2012/0152855 A1 | 6/2012 | Lean et al. |
| 2012/0193297 A1 | 8/2012 | Lean et al. |
| 2012/0193298 A1 | 8/2012 | Lean et al. |
| 2012/0205320 A1 | 8/2012 | Lean et al. |
| 2012/0211432 A1 | 8/2012 | Lean et al. |
| 2012/0318719 A1 | 12/2012 | Lean et al. |
| 2013/0082012 A1 | 4/2013 | Lean et al. |

(Continued)

OTHER PUBLICATIONS

ATP[3] Algae Testbed Fall 2015 Workshop, Large-Scale Algal Cultivation, Harvesting and Downstream Processing . Module 12: Principles of Scaling Up Cultures, Terri Rosov, Nov. 4, 2015; 21 pgs.

(Continued)

*Primary Examiner* — Debbie K Ware
(74) *Attorney, Agent, or Firm* — Fay Sharpe LLP

(57) ABSTRACT

A method and system removes biological contaminants from an algal crop. A flow of an algal crop containing biological contaminants is provided to a hydrodynamic separator (HDS) system. The flow is controlled by a control mechanism, wherein the biological contaminants are concentrated into a first portion of the flow of the algal crop within the HDS system, based on the size of the biological contaminants, and the first portion contains a majority of the biological contaminants in the flow of the algal crop. A second portion of the flow contains a majority of algal in the flow of the algal crop. The flow of the algal crop is split by use of a bi-furcated output of the HDS system. The splitting is between the first portion containing the majority of the biological contaminants in the flow of the algal crop, and the second portion which contains the majority of the algal of the algal crop. The first portion of the flow of the algal crop containing the majority of the biological contaminants is output from a first output of the bi-furcated output, and the second portion of the flow of the algal crop containing the majority of the algal of the algal crop is output from a second output of the bi-furcated output.

20 Claims, 13 Drawing Sheets

(56) References Cited

U.S. PATENT DOCUMENTS

2014/0197113 A1 7/2014 Volkel et al.
2014/0367348 A1 12/2014 Volkel et al.
2014/0367349 A1 12/2014 Volkel et al.
2015/0175454 A1 6/2015 Hsieh et al.

OTHER PUBLICATIONS

ATP³ Algae Testbed Fall 2015 Workshop, Large-Scale Algal Cultivation, Harvesting and Downstream Processing . Module 13: Outdoor Culture Maintenance and Monitoring, Tom Dempster, Nov. 4, 2015; 39 pgs.

CHANNEL CROSS SECTION WITH A STACKED PAIR OF DEAN VORTICES

HYDRODYNAMIC SEPARATION (HDS) FOR REMOVING PROTIST PREDATORS FROM ALGAL CROPS

INCORPORATION BY REFERENCE

The following co-pending and commonly assigned applications, the disclosures of each being totally incorporated herein by reference, are mentioned:
U.S. Patent Publication No. 2009/0050538A1, now U.S. Pat. No. 8,276,760, issued Oct. 2, 2012, to Meng H. Lean, et al., entitled SERPENTINE STRUCTURES FOR CONTINUOUS FLOW PARTICLE SEPARATIONS; U.S. Patent Publication No. 2012/0318719A1, now U.S. Pat. No. 8,869,987, issued Oct. 28, 2014, to Meng H. Lean, et al., entitled SERPENTINE STRUCTURES FOR CONTINUOUS FLOW PARTICLE SEPARATIONS; U.S. Patent Publication No. 2008/0128331A1, to Meng H. Lean, et al., entitled PARTICLE SEPARATION AND CONCENTRATION SYSTEM; U.S. Patent Publication No. 2008/0230458A1, now U.S. Pat. No. 8,875,903, issued Nov. 4, 2014, to Meng H. Lean, et al., entitled VORTEX STRUCTURE FOR HIGH THROUGHPUT CONTINUOUS FLOW SEPARATION; U.S. Patent Publication No. 2009/0114607A1, to Meng H. Lean, et al., entitled FLUIDIC DEVICE AND METHOD FOR SEPARATION OF NEUTRALLY BOUYANT PARTICLES; U.S. Patent Publication No. 2009/0114601A1, to Meng H. Lean, et al., entitled DEVICE AND METHOD FOR DYNAMIC PROCESSING IN WATER PURIFICATION; U.S. Patent Publication No. 2009/0283455A1, to Meng H. Lean, et al., entitled FLUIDIC STRUCTURES FOR MEMBRANELESS PARTICLE SEPARATION; U.S. Patent Publication No. 2009/0283452A1, now U.S. Pat. No. 8,931,644, issued Jan. 13, 2015, to Meng H. Lean, et al., entitled METHOD AND APPARATUS FOR SPLITTING FLUID FLOW IN A MEMBRANELESS PARTICLE SEPARATOR SYSTEM; U.S. Patent Publication No. 2010/0072142A1, to Meng H. Lean, et al., entitled METHOD AND SYSTEM FOR SEEDING WITH MATURE FLOC TO ACCELERATE AGGREGATION IN A WATER TREATMENT PROCESS; U.S. Patent Publication No. 2010/0314323A1, to Meng H. Lean, et al., entitled METHOD AND APPARATUS FOR CONTINUOUS FLOW MEMBRANE-LESS ALGAE DEWATERING; U.S. Patent Publication No. 2012/0193297A1, to Meng H. Lean, et al., entitled METHOD AND APPARATUS FOR CONTINUOUS FLOW MEMBRANE-LESS ALGAE DEWATERING; U.S. Patent Publication No. 2010/0314325A1, to Meng H. Lean, et al., entitled SPIRAL MIXER FOR FLOC CONDITIONING; U.S. Patent Publication No. 2010/0314263A1, now U.S. Pat. No. 8,647,479, issued Feb. 11, 2014, to Meng H. Lean, et al., entitled STAND-ALONE INTEGRATED WATER TREATMENT SYSTEM FOR DISTRIBUTED WATER SUPPLY TO SMALL COMMUNITIES; U.S. Patent Publication No. 2012/0211432A1, to Meng H. Lean, et al., entitled STAND-ALONE INTEGRATED WATER TREATMENT SYSTEM FOR DISTRIBUTED WATER SUPPLY TO SMALL COMMUNITIES; U.S. Patent Publication No. 2010/0314327A1, to Meng H. Lean, et al., entitled PLATFORM TECHNOLOGY FOR INDUSTRIAL SEPARATIONS; U.S. Patent Publication No. 2012/0193298A1, to Meng H. Lean, et al., entitled PLATFORM TECHNOLOGY FOR INDUSTRIAL SEPARATIONS; U.S. Patent Publication No. 2012/0074074A1, to Meng H. Lean, et al., entitled SELF-CLEANING SCREEN SYSTEM AND METHOD; U.S. Patent Publication No. 20120152814A1, now U.S. Pat. No. 8,268,169, issued Sep. 18, 2012, to Meng H. Lean, et al., MEMBRANE BIOREACTOR (MBR) AND MOVING BED BIOREACTOR (MBBR) CONFIGURATIONS FOR WASTEWATER TREATMENT; U.S. Patent Publication No. 2012/0152855A1, to Meng H. Lean, et al., entitled SYSTEM AND APPARATUS FOR SEAWATER ORGANICS REMOVAL; U.S. Patent Publication No. 2012/0145546A1, now U.S. Pat. No. 8,518,235, issued Aug. 27, 2013, to Armin R. Volkel, et al., entitled ALL-ELECTRIC COAGULANT GENERATION SYSTEM; U.S. Patent Publication No. 2012/0145647A1, to Armin R. Volkel, et al., entitled ELECTROCOAGULATION SYSTEM; U.S. Patent Publication No. 2015/0175454A1, to Huangpin B. Hsieh, et al., entitled RECYCLING ACTIVATED SLUDGE BY HYDRODYNAMIC SEPARATOR (HDS) TO ENABLE HIGH MLSS BIOREACTOR TO PROCESS HIGH INFLUENT FLOW AND/OR HIGH STRENGTH WASTEWATER; U.S. Patent Publication No. 2014/0367349A1, to Armin R. Volkel, entitled HYDRODYNAMIC SEPARATION USING HIGH ASPECT RATIO CHANNELS U.S. Patent Publication No. 2014/0367348A1, to Armin R. Volkel, entitled HDS CHANNEL EXIT DESIGNS FOR IMPROVED SEPARATION EFFICIENCY; U.S. Patent Publication No. 2014/0197113A1, to Armin R. Volkel, entitled SYSTEMS AND APPARATUS FOR REMOVAL OF HARMFUL ALGAE BLOOMS (HAB) AND TRANSPARENT EXOPOLYMER PARTICLES (TEP); U.S. Patent Publication No. 2013/0082012A1, now U.S. Pat. No. 8,852,446, issued Oct. 7, 2014, to Meng H. Lean, entitled PLATELET EXTRACTION FROM BLOOD; U.S. Patent Publication No. 2012/0205320A1, to Meng H. Lean, entitled DESALINATION USING SUPERCRITICAL WATER AND SPIRAL SEPARATION; U.S. Patent Publication No. 2011/0108491A1, to Meng H. Lean, entitled DESALINATION USING SUPERCRITICAL WATER AND SPIRAL SEPARATION; and U.S. Patent Publication No. 2005/0247564A1, now U.S. Pat. No. 7,534,336, May 19, 2009, to Armin R. Volkel, et al., entitled CONTINUOUS FLOW PARTICLE CONCENTRATOR.

BACKGROUND

A common concern when growing algae is protection of the algae from biological contaminants. Within the algae growing industry this is known as crop protection. The current state of scaled algae production, typical for biofuels, for example, is to first start a small pure culture (axenic or uni-algal) on an agar plate or slant in sterile laboratory conditions. Large-scale algae production, as shown in FIG. 1, will commonly progressively scale up batch (i.e., non-continuous) cultures of algae from culture tubes or flasks (<100 ml), to columns (~100 ml-800 ml) 100, to panels (15 L to 1,500 L) 102 or outdoors, and finally as shown as in FIG. 2 to outdoor ponds (1,000-150,000+L; and/or photobioreactors) 200. Due to the continuous threat of biological contamination, algae production has mostly been limited to batch cultivation, as opposed to the more productive continuous cultivation. A hurdle to continuous algae cultivation is prevention or minimization of biological contamination.

Each stage of the scale-up sequence provides the inoculum (i.e., the substance used for inoculation) for the subsequent stage, and care must be taken to identify biological contamination and confirm the health of the culture prior to transfer and continued scale-up. Signs of contamination include, among others, discoloration, unusual odor, biofouling, foam production, or auto-flocculation. Causes of biological contamination include, among others, the presence of predator protists (amoeboids, ciliates and flagellates), non-beneficial bacteria, fungi, filamentous cyanobacteria, or undesirable species of algae.

After inspection (commonly at the microscopic level) to confirm that the culture is sufficiently free of biological contaminants at the end of the batch culture period (which can take anywhere from a few days to a few weeks depending on growth conditions), the contents of a column or panel is then transferred to a panel or pond (respectively) that only contains growth media, and the process continues. Carbon dioxide and nutrients (e.g., nitrogen, phosphorus, and/or other micronutrients) in excess allow for uninhibited logarithmic growth (log-growth) until the concentration of algae becomes self-limiting due to shading. With the final cultivation step for algal growth for biofuel production, the crop is starved of nitrogen, stimulating the storage response that results in hyper-accumulation of carbon as an intracellular lipid, at which point the crop is harvested. Harvesting involves dewatering the entire contents of the pond or photo-bioreactor and passing through a combination of centrifuges, settlers, and/or dissolved air floatation technologies to concentrate and collect the algal biomass.

After inoculation of any step, the sheer mass of algae is relied on to out-compete any biological contaminants during log-growth phase, as long as substantially the entire volume is transferred to the next stage or harvested expeditiously. Still, both the batch inoculum stages and final pond or photo-bioreactor stage are subject to biological contamination. If there are enough of these unwanted organisms, and/or they grow fast enough (Rotifers can consume 70,000 algal cells per day, for example), the inoculum batch must be discarded or the pond or photo-bioreactor must be harvested prematurely before the entire crop is completely infected and useless. A particular hurdle to algae cultivation, including continuous cultivation, is therefore prevention or minimization of predation.

BRIEF DESCRIPTION

A method and system removes biological contaminants from an algal crop. A flow of an algal crop containing biological contaminants is provided to a hydrodynamic separator (HDS) system. The flow is controlled by a control mechanism, wherein the biological contaminants are concentrated into a first portion of the flow of the algal crop within the HDS system, based on the size of the biological contaminants, and the first portion contains a majority of the biological contaminants in the flow of the algal crop. A second portion of the flow contains a majority of algal in the flow of the algal crop. The flow of the algal crop is split by use of a bi-furcated output of the HDS system. The splitting is between the first portion containing the majority of the biological contaminants in the flow of the algal crop, and the second portion which contains the majority of the algal of the algal crop. The first portion of the flow of the algal crop containing the majority of the biological contaminants is output from a first output of the bi-furcated output, and the second portion of the flow of the algal crop containing the majority of the algal of the algal crop is output from a second output of the bi-furcated output.

DETAILED DESCRIPTION

Current research for crop protection has focused primarily on the use of antibiotics extracted from other microorganisms. As an alternative, the present application discloses the use of Hydrodynamic Separation (HDS) technology to separate predators from algal cultures, salvaging contaminated batches of inoculum, contaminated crops of whole ponds or photo-bioreactor systems, and/or to allow continuous cultivation by removing predators before they can proliferate.

With properly sized and configured HDS channels and proper process control operations and systems, predators (based on harvest efficiency of the HDS channels) and a certain amount of algae (based on volumetric flow split) is removed by HDS. Below are the comparative sizes of protist predators and commonly grown algal strains.

Most of these biological contaminants (namely, the predator protists listed in Table 1) are significantly larger than the algae being grown (Table 2).

TABLE 1

Biological contaminants - sizes of predators of algae.

| name | size, um |
|---|---|
| Paramecium | 50-330 |
| amoeba | 250-750 |
| rotifer | 100-500 |

TABLE 2

Common algae species.

| genus | size, um | Application |
|---|---|---|
| Scenedesmus | 5-12 | biohydrogen, biodiesel, bioethanol, wastewater treatment |
| Chlorella | 2-10 | Dietary supplement, biofuels, wastewater treatment |
| Chlamydomonus | 5-10 | biohydrogen, biopharmaceuticals |
| Nannochloropsis | 2-3 | Biofuels |
| Porphyridium | 5-16 | biofuels, biopharmaceuticals |
| Dunaliella | 9-11 | biofuels, carotene |

The employed Hydrodynamic Separation (HDS) technology separates particles based on size. Therefore HDS is useful in selectively removing biological contaminants.

Hydrodynamic separation (HDS) of suspended particles using curved channels can offer advantages in many applications. It is a fast continuous flow technology that can handle particles, including neutrally and near neutrally buoyant particles, without the need of a physical barrier or the addition of chemical aids. To get the best benefit for a specific application, it is useful to understand the design parameters that control cut-off size, flow rate, pressure drop, etc. The following concepts relate to the role of the channel aspect ratio on the focusing dynamics of the hydrodynamic separator.

Figure 2:
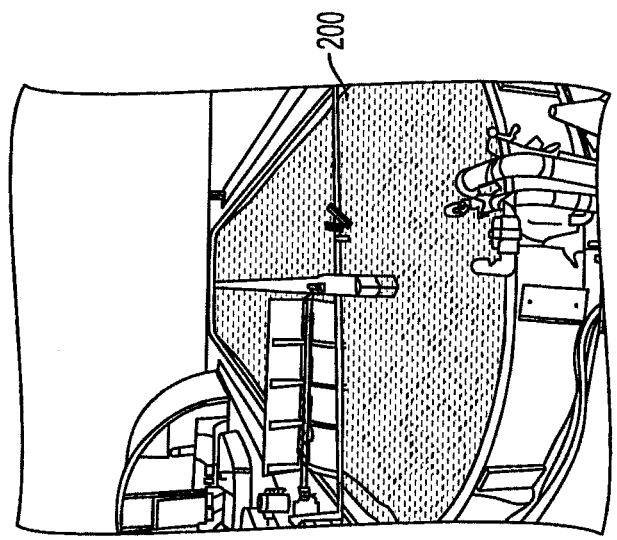
FIG. 2 depicts an outdoor pond and/or photo-bioreactor holding algae growth for crops.
Figure 1:
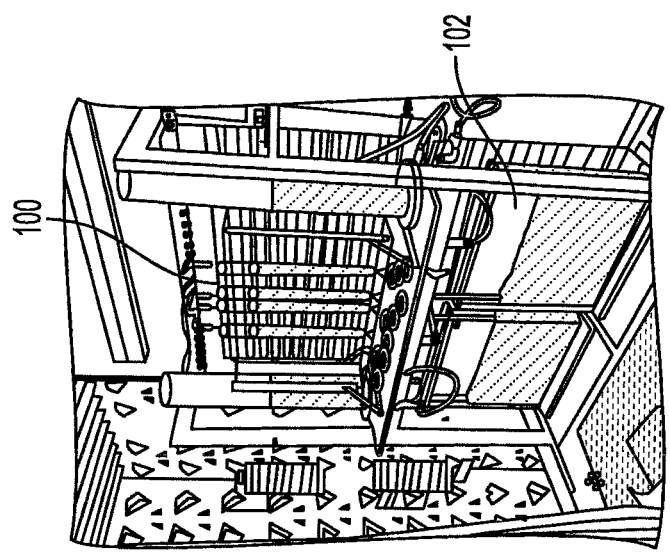
FIG. 1 is an illustration of cultures of algae in flasks and columns.
Figure 3:
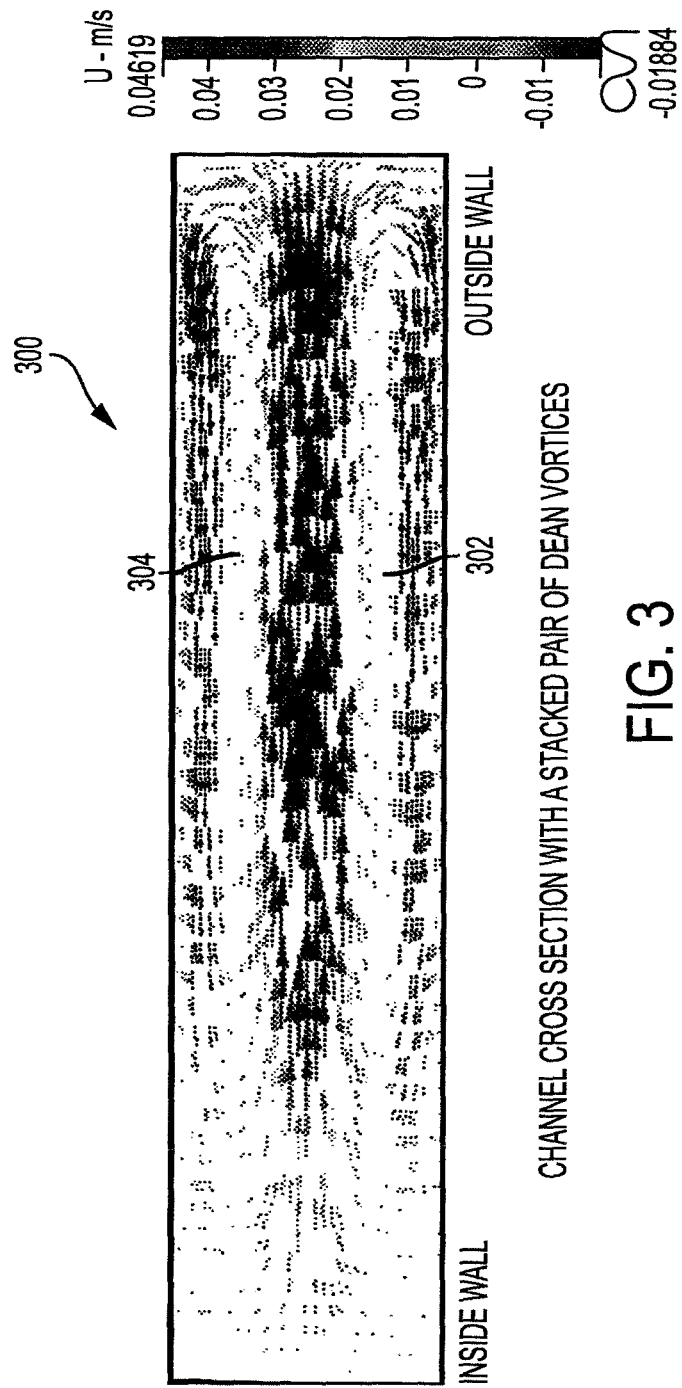
FIG. 3 shows a cross-section of a channel.

Referring now to FIG. 3, because of the generation of centrifugal forces on the fluid or liquid flowing through the channel in certain circumstances, transverse flow patterns emerge. Under certain flow conditions and geometrical constraints, these transverse flow patterns emerge as a pair of Dean vortices. As shown, a fully developed Dean vortex pair 302, 304 in the cross-sectional plane of a curved channel 300. Particles entrained in such a flow are spiraling around these vortex cores as they move along the channel. In certain locations, a combination of shear and inertia forces push the particles closer to the vortex centers, causing a dynamic focusing of the particles into a band around the vortex cores.

Figure 4A:
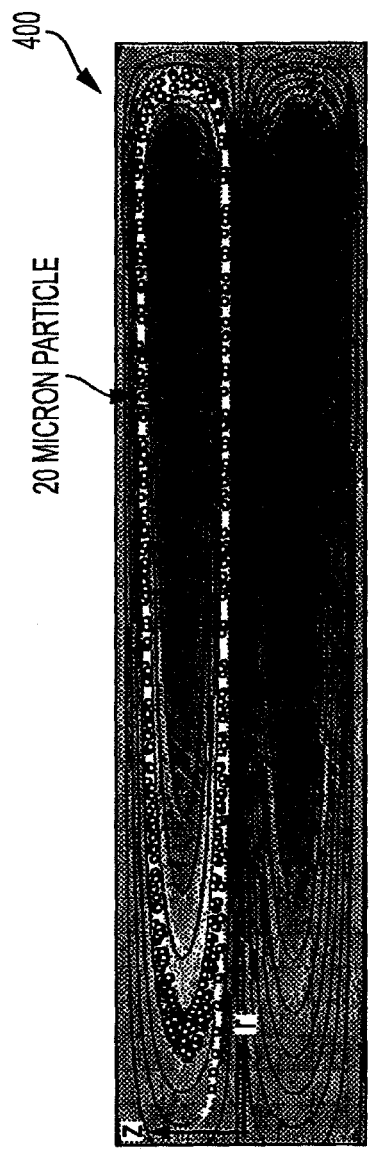
FIGS. 4A and 4B show a cross-section of a channel.
Figure 4B:
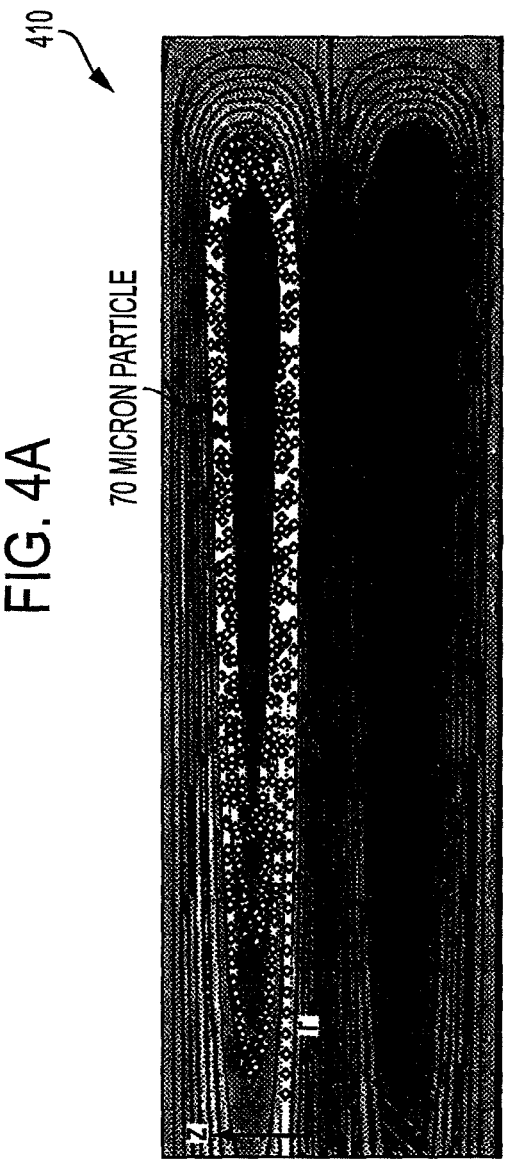

To illustrate, with reference to FIGS. 4A and 4B, because of size dependence of the lift forces, only particles exceeding a certain size (i.e., cut-off size), which depends on the channel geometry and flow rate, are affected enough to become part of the concentrated band. FIGS. 4A and 4B show a projection of particle trajectories on a cross-sectional area of curved channels 400 and 410 each with aspect ratio A=4.55. The solid lines indicate projections of streamlines onto the same cross-sectional area. The particles are not shown to scale, only representatively for ease of illustration. As shown in FIG. 4A, a 20 micron particle is barely affected by the shear and inertia forces and closely follows the stream lines. No focusing effect is visible. However, as shown in FIG. 4B, a 70 micron particle experiences stronger shear and inertia forces near the outside wall, where it crosses streamlines towards the Dean vortex core. There is dynamic focusing toward the vortex core.

Figure 5:
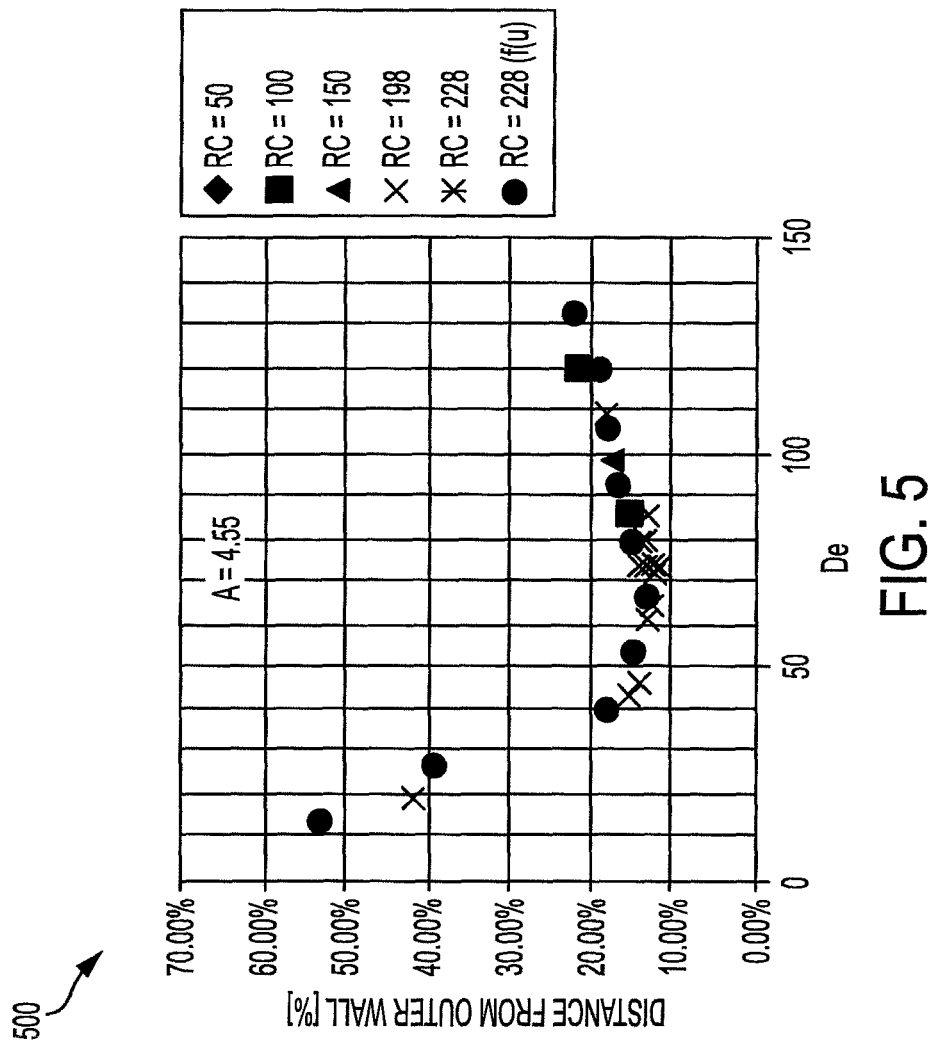
FIGS. 5, 6 and 7 show Computation Fluidic Dynamics (CFD) simulation results.
Figure 6:
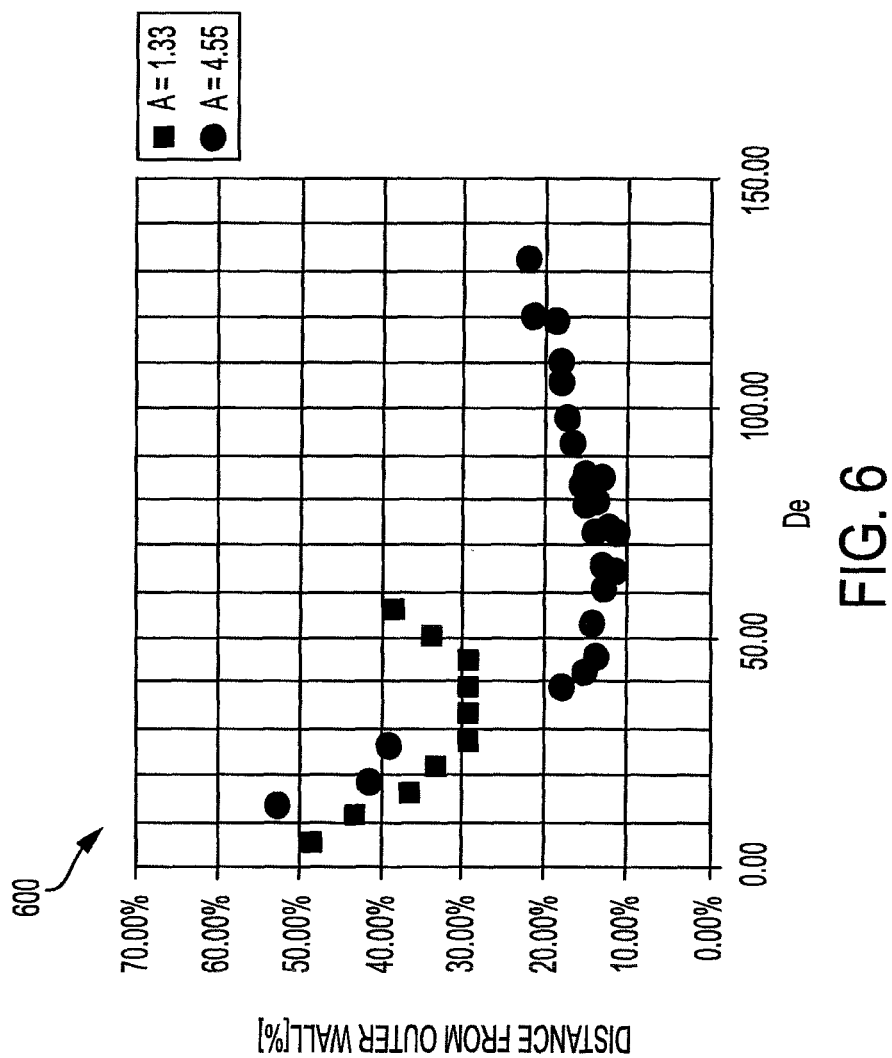

In low aspect ratio (A=width/height) channels, focusing is dynamic, i.e. for each complete loop the particle goes around a vortex center it is pushed a bit closer to the vortex center. FIGS. 4A and 4B describes the observed physics in channels with not too large an aspect ratio (e.g. Ookawara, D. Street, K. Ogawa, Chem. Eng. Sci., 61, 3714-3724, (2006)) (A=4/3 or 1.33), H. B. Hsieh, A. R. Volkel, N. E. Chang, A. Kole, K. Melde, F. Torres, Water Science & Technology—Water Supply, 13(2), 524-530, (2013) (A=5/1.1 or 4.55) each incorporated herein in their entirety by reference). The flow field in the channels under consideration ($D_H \ll R_C$, where the hydraulic radius $D_H$ is the characteristic length scale of the channel cross-section and $R_C$ is the radius of curvature) is completely described by the Dean number $$De = Re\sqrt{\frac{D_H}{2R_C}} = 2\left(\frac{\bar{v}H}{v}\right)\left(\frac{H}{R_C}\right)^{1/2}(\alpha)^{3/2},$$

which combines the Reynolds number $$Re = \frac{\bar{v}D_H}{v} = \frac{\bar{v}2\alpha H}{v}$$

with information on the radius of curvature, and $$\alpha = \frac{1}{1+1/A}$$

is a function of the aspect ratio A. H is for height of the channel, $v$ is kinematic viscosity, and v is for velocity. For a fixed aspect ratio A=width/height, the relative distance of the Dean vortex centers from the outside wall $$d_r = \frac{\text{outside wall location} - \text{Dean vortex loaction}}{\text{channel width}}$$

falls on a universal curve. Chart 500 of FIG. 5 shows $d_r$ as function of Dean number for A=4.55. The different markers are for channels with different radius of curvature $R_C$ and varying flow rate (solid circle).

$d_r$ has a well-defined minimum at a finite Dean number, but both the closest distance to the wall, as well as the Dean number for this to happen, are functions of the aspect ratio A. With increasing A, the minimal distance to the outside wall is decreasing and occurs at a larger Dean number (De). Chart 600 of FIG. 96 shows a relative distance $d_r$ of vortex core from outer wall as function of Dean number (De). The different markers are for channels with two different aspect ratios A.

It is understood a Dean number is a dimensionless group in fluid mechanics, which occurs in the study of flow in curved pipes and a Reynolds number is the ratio of internal forces to viscous forces, to predict the flow velocity at which turbulence will occur.

When using the curved channel as a separator and/or concentrator of suspended particles by placing a flow splitter at the exit, it is advantageous to have the particle band forming as close to the outside wall as possible to minimize the amount of liquid diverted with the particle stream at the flow splitter. In other words, the closer the particle bands can form relative to the outside wall, the higher the split ratio can be achieved. Besides its impact on the band location, the aspect ratio also provides a control parameter for the flow rate of the liquid and/or the radius of curvature of the channel, hence allowing the optimization of channel geometries for specific applications.

High aspect ratio channels allow for different results. In one form, once the aspect ratio exceeds about 7, the particle focusing dynamics changes. That is, in at least one form, any particle that is carried for the first time close to the outside wall will remain there, i.e. the final band forms within the first loop of the particles around the Dean vortex center. Of course, the aspect ratio may vary. For example, in some forms, it may be 7.5, 8, 15 or any value between 7.5 and 15, such as between 8 and 15. It may exceed 15. In at least some forms, any aspect ratio exceeding a value of about 7 is acceptable. Also, the Dean number may vary. In at least one form, the flow is adjusted such that the Dean number is between 30 and 100 inside the channel. In some other forms, flow may be adjusted such that the Dean number is between 60 and 80 inside the channel.

Figure 7:
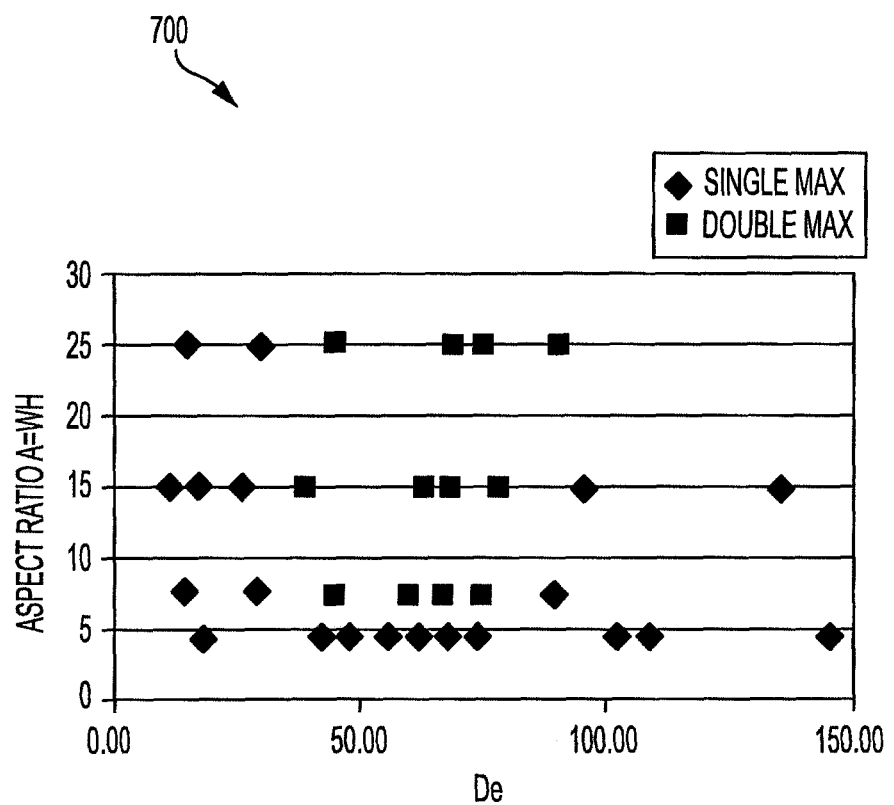

This change in particle focusing behavior is accompanied by additional maxima in the transverse vorticity. In this regard, besides the vorticity maxima at the two Dean vortex cores (as shown in FIGS. 3, 4A and 4B), two additional maxima appear near the outside wall. Chart 700 of FIG. 7 shows the occurrence of these additional maxima in the transverse vorticity as a function of Dean number and aspect ratio. Once the aspect ratio exceeds about 7, there is a wide range of Dean numbers (De) for which these additional vorticity maxima exist and a narrow particle band near the outside wall forms. As shown, the number of maxima of the transverse vorticity component (per half channel) as a function of Dean number and aspect ratio. Diamond markers indicate single maximum, and rectangle markers represent double maxima.

It will be appreciated that advantages are realized when using channels with larger aspect ratio. One reason these advantages can be realized is because effective particle separation cut-off size is mainly determined by the height of the channel (while the width and operational pressure also contribute). Thus, making the channel wider (thus higher aspect ratio), while maintaining the channel height and average flow speed, allows for increased volumetric flow rate per channel without significantly modifying the Dean and Reynolds numbers. Also, no significant increase of pressure head is required to operate the widened channel.

Another advantage is realized by increasing the channel aspect ratio which causes the particle band to form closer to the outside wall, allowing for a better clean stream to concentrate stream ratio.

Further advantages are realized by pushing the aspect ratio beyond about 7 which causes particle focusing during the first loop of the particles around the Dean vortex core. This allows high aspect ratio channel to have good separation with much shorter channel length than is possible for low aspect ratio channel, effectively reducing the energy needs for separation or the amount of materials required to construct the channels. On the other hand, more liquid can flow though the high aspect ratio channels per unit time, effective increasing the throughput.

In configuring devices according to the presently described embodiments, consideration should be given to several factors. For example, increasing the channel width increases the time (or the distance along the channel) for a particle to loop around the vortex core once, although the typical resident time for particles within the current channel scale (i.e. radius of curvature) are very short (on the order of 1-3 seconds). Further, increasing the aspect ratio beyond about 7 gives a large advantage in the channel length required to achieve good separation, because of the change in focusing dynamics. However, if increasing channel width beyond an aspect ratio of 7, the configurations may also take into account the optimization of channel length vs. flow rate per channel, which impacts footprint, cost of manufacturing, and maintenance of a multi-layer channel stack system.

Figure 8A:
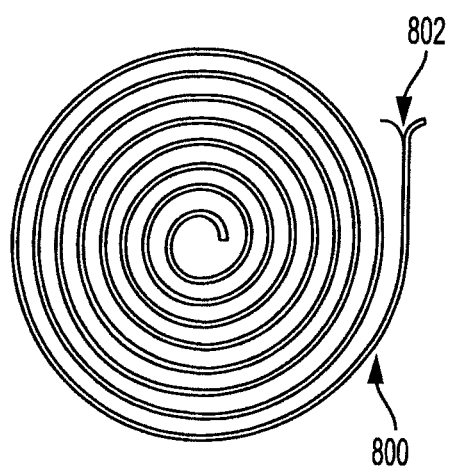
FIGS. 8A-8D are examples of HDS channels.
Figure 8B:
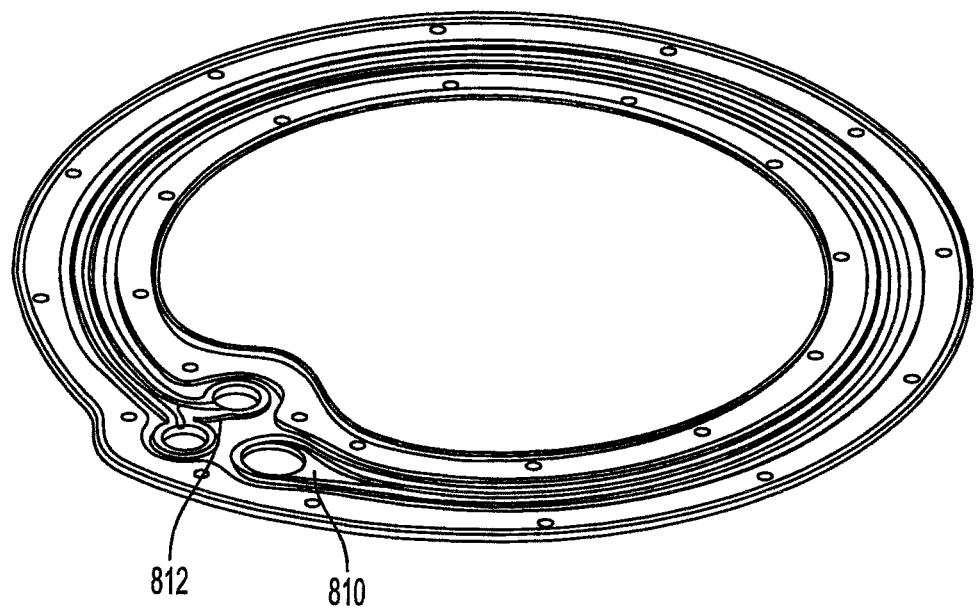
Figure 8C:
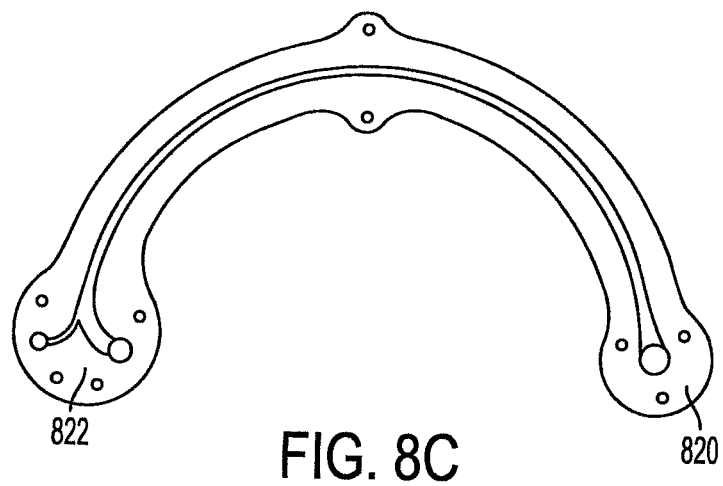
Figure 8D:
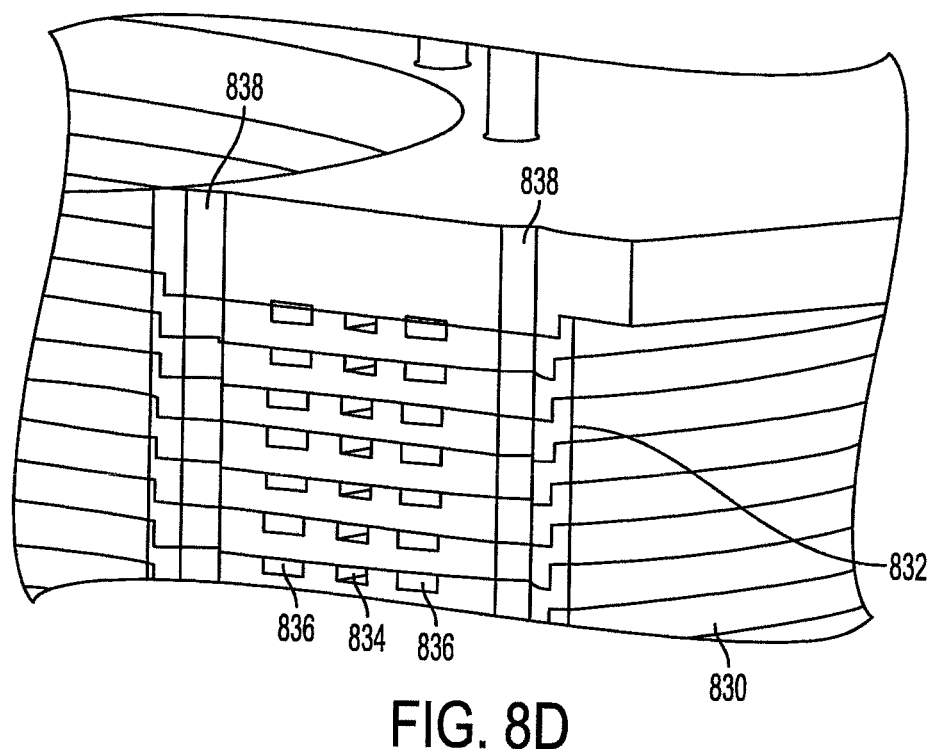

The foregoing has described the HDS concepts in connection with a curved channel. Below are other examples of designs in example operational scenarios that improve HDS separation efficiency for selected implementations. Of course, it should be appreciated that such examples may also include a variety of different configurations of curved channel devices that utilize various hydrodynamic forces, some of which are described above and hereinafter, to separate particles into portions of the field flow and/or bands of particles for purposes of separation. Examples of such curved channel HDS devices (or portions thereof) are illustrated in FIGS. 8A through 8D. FIG. 8A shows a representative view of a curved channel device 800 taking the form of a single channel spiral device that includes multiple turns. The device 800 has a bi-furcated outlet region 802. FIG. 8B shows a curved device 810 having a single channel, full turn configuration where the channel spans between 180 degrees and 360 degrees (e.g. close to 360 degrees as shown). The device 810 has a bi-furcated outlet region 812. FIG. 8C illustrates a curved device 820 having a single channel and a half turn configuration. The device 820 has a bi-furcated outlet region 822. FIG. 8D shows a stack 830 of a plurality of curved hydrodynamic separation devices 832. Also shown in FIG. 8D are channels 834, gaskets or sealing elements 836, and apertures 838.

It should be appreciated that such devices (e.g. those shown in FIGS. 8A-8D) may be incorporated in a system for separating particles in fluid (e.g. liquid). Such a fluid in certain embodiments include an algal crop or culture (such as but not limited to those mentioned in Table 2), that has or is thought to have biological contaminants including but not limited to those mentioned in Table 1. Such a system may include control elements (e.g. control modules, processors, actuators, sensors, . . . etc.) to control the flow of the fluid to achieve the contemplated separation in the system.

Thus the described embodiments provide a fluid splitting system at the outlet of the various HDS devices that is transparent to the fluid flow. That is, implementation of the presently described embodiments does not typically cause dispersion or otherwise compromise the integrity of a focused particle band or group of particles, does not create undue turbulence, and does not cause excessive pressure fluctuations that would impair the desired fluid flow. The presently described embodiments related to removal of the biological contaminants allow for adaptability of the split of fluid flow, e.g. in a range from a 10:90 split to a 90:10 split. Suitable flow sensing and computer feedback control may also be applied to the system.

The presently described embodiments may take a variety of forms, as those of skill in the art will appreciate. As described herein, the presently described embodiments may include static or passive mechanisms or subsystems. These mechanisms could also be modular and interchangeable to provide for preset fluid split divisions (e.g., 10:90 to 90:10). In other forms the system is adjustable and variable. In still another form the system allows for differential pressure control at the outlets to facilitate the flow of varying size particles or particle bands in the respective channels or paths. The system may also include various sensing and feedback control to allow for the enhanced splitting of the fluid flow. For example, sensors (e.g., optical sensors, flow sensors, pressure sensors, temperature sensors, viscosity sensors, etc.) may be placed in the system prior to or after the point of splitting or bifurcation. A feedback signal may be sent to a splitting mechanism to maximize band capture and fluid recovery in the channels. A sensor may also be provided along the channel to detect velocity variations. This data may then be used to feedback to necessary pumps to maintain a desired (e.g., constant) flow rate, and hence, velocity. A sensor could also be provided to adjust flow rate in each channel to minimize band dispersion and to maximize flow recovery. Sensors may be used to correct fluidic operation, and sensors may be used to correct for adjustment in operation parameters.

It should be appreciated that these types of sensing and feedback control devices may be implemented in a variety of different manners within the system to achieve the sensing and feedback objectives noted herein and others. In this regard, these types of devices may be implemented using different hardware configurations and/or software techniques that are suited to the environment and system configuration.

Figure 9:
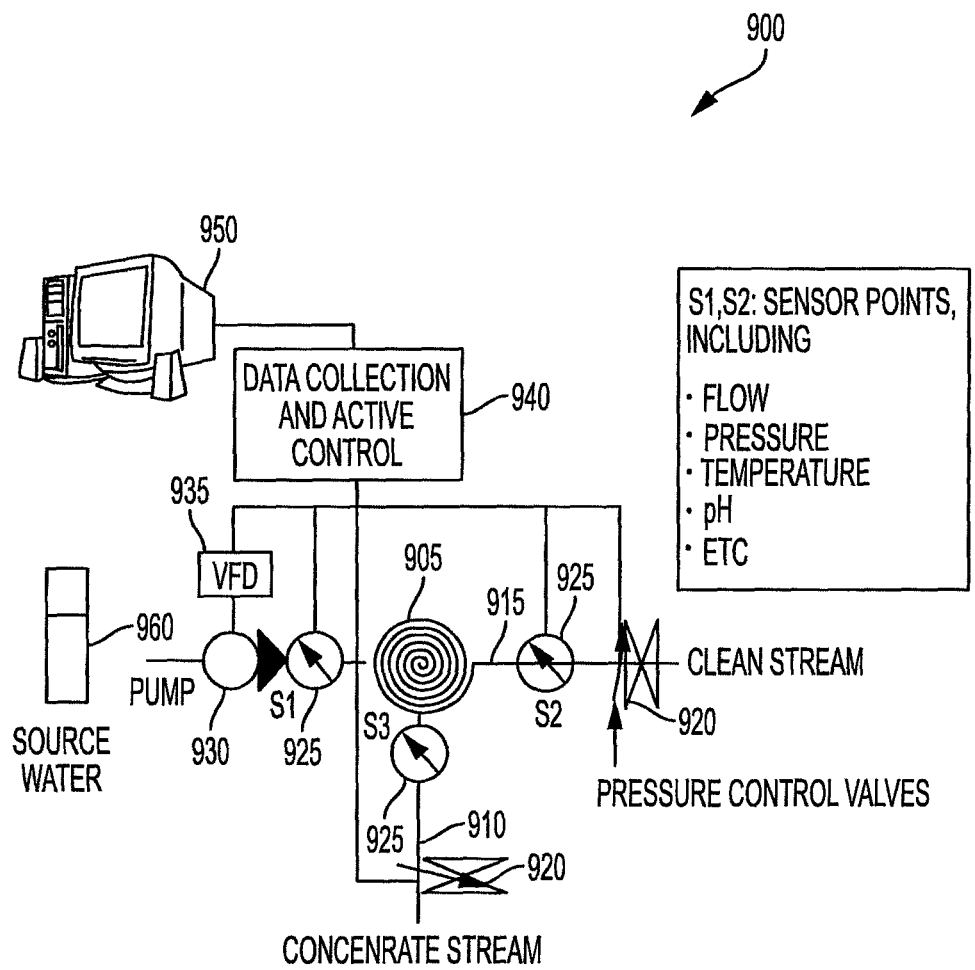
FIG. 9 shows an HDS control system.

Turning now to FIG. 9 depicted is a system 900 configured to control operation of the HDS channel arrangements. This system may incorporate the above noted concepts, components and/or devices. The system 900 includes a curved channel device 905, where the shown spiral is a mere example representation of a HDS device and may take a variety of forms including those described herein. Also shown are an output stream (i.e., a concentrate stream) 910 and an output stream (i.e., a non-concentrate stream) 915. Pressure control valves 920 and sensors 925 are also shown in the system. More particularly, sensors S1 (925), S2 (925), and S3 (925) are illustrated. Where sensor S1 (925) uses output from pump 930, sensor S2 (925) is provided in output stream 915, and sensor S3 (925) is found in output stream 910. In certain embodiments, the sensors (e.g. S2 (925), S3 (925) are optional and configured as needed. Similarly, pressure control valves 920 can both be installed, only one installed, or neither installed dependent upon the implementation. A pump 930 may be used to pump fluid from a fluid source 960 into the system 900, so that fluid having particles is input to the curved channel device 905 for processing according to the presently described embodiments. Further, a variable frequency drive (VFD) for controlling the pump 930, a data collection and active control system 940 and a user interface 950 are illustrated. It should be appreciated that the system 900 may be used to measure a variety of parameters including flow, fluid velocity, pressure, temperature, pH, etc. Knowledge of these parameters allow the control system 940, along with actuators such as the pump 930 and pressure control valves 920, to operate the system at desired conditions according to the presently described embodiments.

In one embodiment a system of the example of FIG. 9 or a similar system, a hydrodynamic separation device is implemented and is comprised to remove biological contaminants from an algal crop or culture. In this design an inlet for the algal containing fluid, a curved channel having a width and height and being configured to receive the fluid such that at least one pair of Dean vortices is formed in the fluid, wherein interaction with flow patterns causes particles to form a concentrated band near an outer wall (e.g. an outer side wall) of the channel, wherein the flow is adjusted such that the Dean number in the channel is between approximately 30-100 and in certain embodiments between approximately 60-80, and further wherein a ratio of the width to the height of the channel is at least 7 and in certain embodiments is approximately 15, and an outlet is configured to allow the concentrated stream containing the biological contaminants to exit the channel on a first path and remaining algal crop or culture fluid to exit the channel on a second path.

A band of particles (biological contaminants) larger than the cut-off size (which can be less than 10 um, typically 10 um-100 um, or larger than 100 μm) forms on the outside of the HDS channel. The flow is then split at the end of the channel in order to separate the band of particles (biological contaminants, concentrates) from a fluid (contaminated algae culture). The flow split is a fraction of total flow, and is variable based on the geometry of the channel and split design. This flow split could be anywhere in the range of 10:90 to 90:10, as well as 50:50 (with the second value of each ratio containing the band of larger particles, which is located on the outer radius of the channel). The ideal split has as little fluid as possible go with the predatory organisms. In reality, this means an approximately 80:20 split. Other split ratios may be necessary depending on the concentration of the predatory organisms is desirable and could be approximately 90:10, 70:30 or 60:40 as well. Particles smaller than the cut-off size (algae) will also be separated by the geometric split, but only proportional to the split ratio, as these particles are not affected by hydrodynamic separation. For example, an HDS system with a 20 μm cut-off size and a 70:30 flow split and capable of 90% capture of particles greater than 100 μm will have 95% of the rotifers, paramecium and amoebas and 30% of the algae all in 30% of the flow.

In one embodiment, system 900 is used intermittently as needed to 'clean' or 'polish' or remove biological contaminants from a batch culture or cultures as needed to salvage that culture. This saves considerable time, given that it takes anywhere from a few days to a few weeks to replace a given culture, and considerable cost, especially with pond systems, as growth media is expensive and a contaminated pond requires a large quantity of salts and nutrient.

The proposed technology is however not limited to intermittent use, and may be configured and operated to enable continuous algae culture. The system(s) 900 are also not limited to being used to remove biological contaminants from algal cultures of columns, panels, or ponds—this technology is applicable to all algal culture systems where the removal of biological contaminants is desirable.

Figure 10:
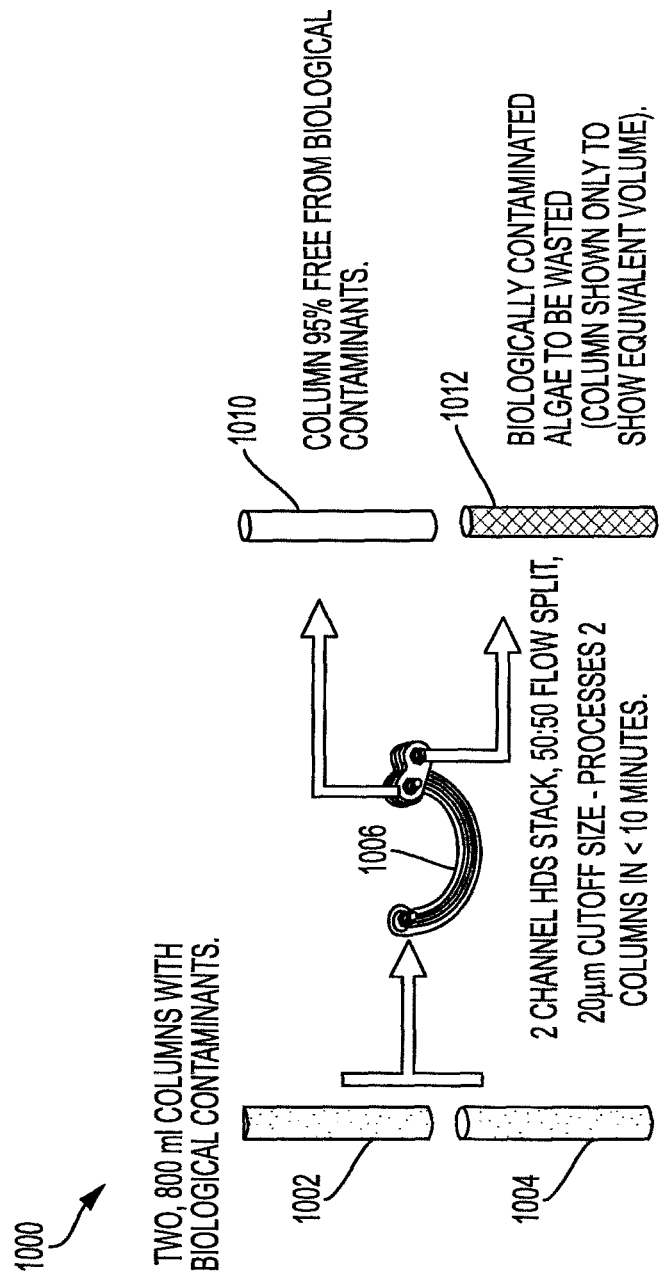
FIGS. 10, 11 and 12 illustrate HDS arrangements for removal of biological contaminants according to the present application.
Figure 11:
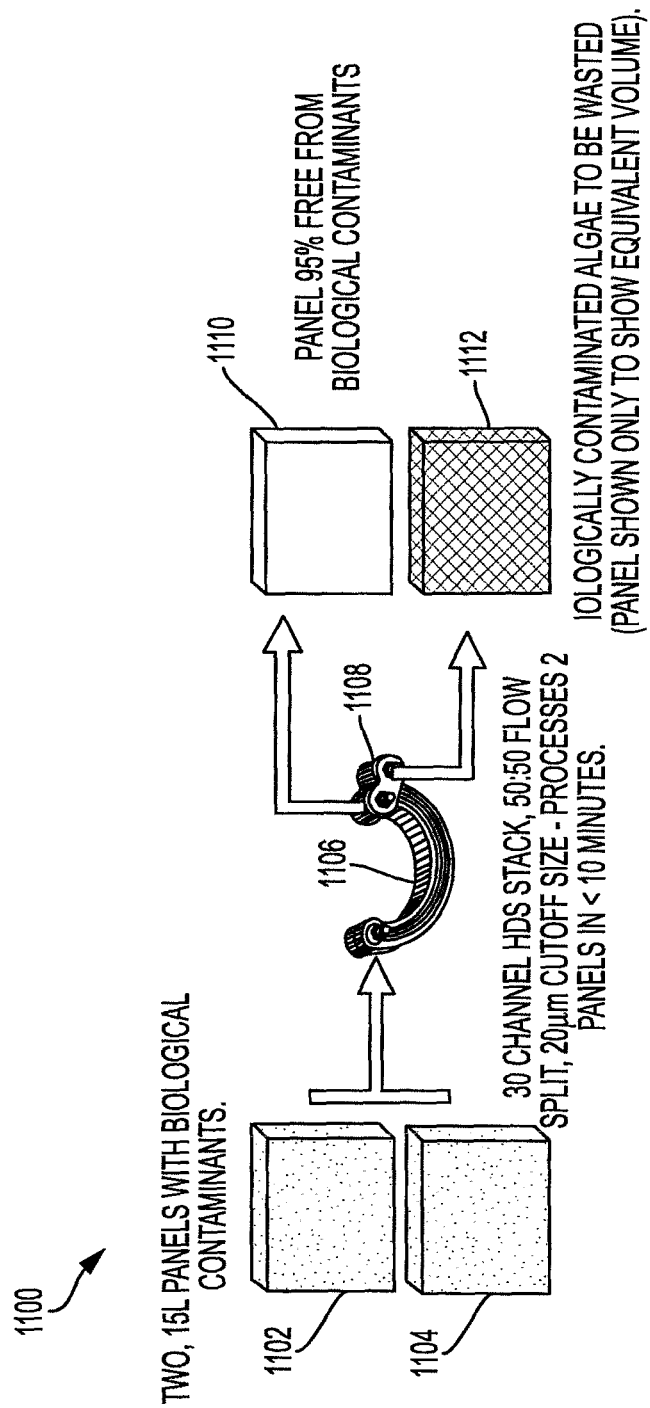
Figure 12:
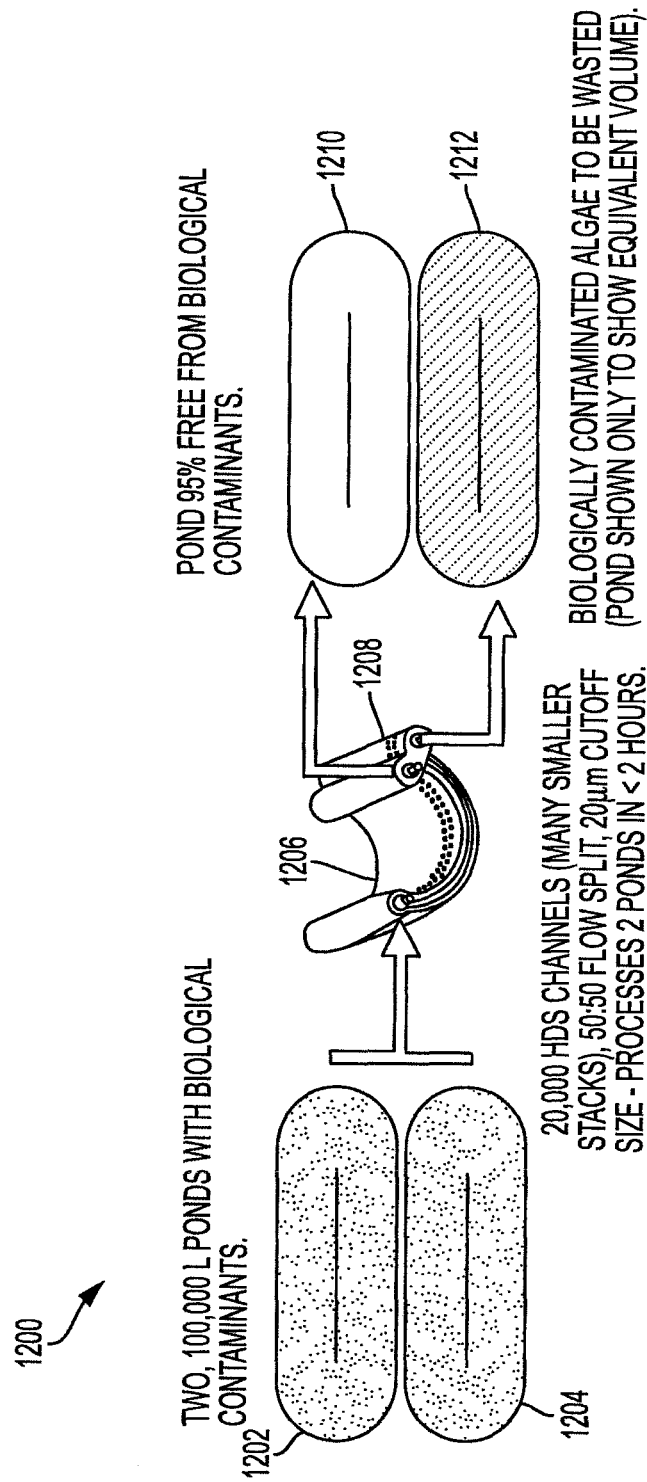

Three exemplary HDS system designs at different system size/scale are provided herein (FIGS. 10, 11 and 12).

In FIG. 10, shown is a system 1000 which includes two 800 milliliter algal columns 1002, 1004 in which biological contaminants exist. An HDS arrangement 1006 is configured to receive the water with algae and biological contaminants. In this embodiment the HDS system 1006 includes two-channel HDS stacks, with a 50:50 flow split, and having a 20 μm cut-off size for the particles within the water from the columns. The processing for the two columns would take less than approximately 10 minutes. Passing through a bi-furcated output 1008, a first column 1010 filled with algal water wherein the column 1008 is 95% free from biological contaminants compared to the water prior to processing. A second column 1012 shown just for convenience includes the water with the concentrated biologically contaminated algae, and which will be discarded as waste.

Turning to FIG. 11, shown is a system 1100 wherein two 15 liter algae-filled panels 1102, 1104 having biological contaminants. The water from these panels is provided to an HDS system 1106. This particular HDS system is a 30-channel HDS stack, with a 50:50 flow split and a 20 μm cut-off size for the particles. The processing of the two panels will occur within less than 10 minutes. The bifurcated output 1008 provides a stream which fills panel 1010 which is algal filled and 95% free of biological contaminants compared to the water prior to the processing. Panel 1012 is provided as an example where the biologically contaminated algal which is to be discarded as waste is shown.

Turning to FIG. 12, a still further embodiment similar to the above embodiments provides a system 1200 where two 100,000 liter algal growing ponds 1202, 1204 have biological contaminants. This contaminated water is provided to an HDS system 1206, which has 20,000 HDS channels (in multiple smaller stacks), each having approximately 50:50 flow split and with a 20 μm cut-off size of the particles being processed. This arrangement is capable of processing the two ponds in under two hours. The HDS channels of system 1206 include bifurcated output 1208 from which a contaminant diminished flow is received by pond 1210, the pond 1210 being 95% free of the biological contaminants compared to the water prior to the processing. The exemplary pond 1212 shows the flow which has the majority of the biologically contaminated algae. The pond is shown only to show equivalent volume.

The following HDS system design boundaries are proposed for a single process unit (column, panel, or pond):
Channel Details
  Particle cut-off size—10-100
  Operating pressure: 1-40 psi
  Curved flow path: 180-360 degrees
  Flow rate per channel: 0.1-1 lpm Mass capture (separation efficiency) for biological contaminants: 80-95%
Flow split: 50:50 to 90:10
System Details

| Application: | Volume, L | # of channels for system | Process time, minutes |
|---|---|---|---|
| 1 Column | 0.1-0.8 L | 1-10 | <1-10 |
| 1 Panel | 15-1500 L | 1-1,000 | 15-300 |
| 1 Pond | 1,000-150,000 L | 5-10,000 | 15-300 |

Figure 13:
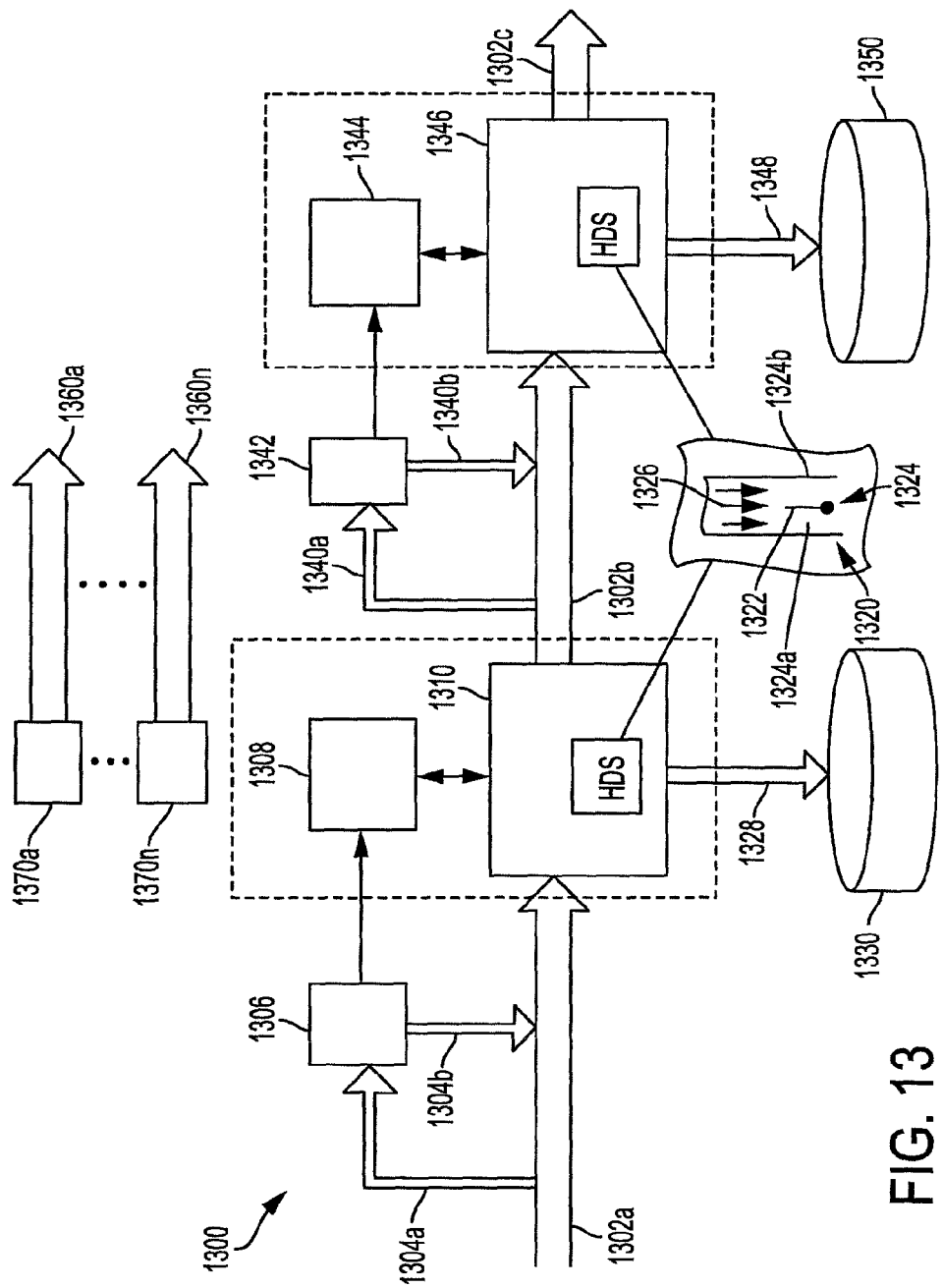
FIG. 13 describes a system to control flow operation for maintaining algae growth.

FIG. 13 illustrates a continuous flow algal cleaning system 1300. In this arrangement, a flow of fluid (e.g., water) from a source such as those sources found in FIGS. 10, 11 and 12 is represented by flow 1302a. Flow 1302a will contain algae and biological contaminants. Initially a portion of the flow is diverted via diverter path 1304a, which is provided to a test module 1306. The water which has been diverted is tested in appropriate testing equipment to provide data regarding the biological contamination, which may include the type of biological contaminants, size of the biological contaminants, concentration and other data regarding the biological contamination within the water flow 1302a. Testing can also include testing for discoloration, unusual odor, biofouling, foam production, or auto-flocculation using optical sensors, air sensors, imaging devices to confirm the biological contaminants present, among other known testing apparatuses. The fluid not needed for the testing is re-supplied via return path 1304b to the main water flow 1302a. The test module 1306 provides the information gathered to a control module 1308 which communicates with HDS system 1310. This arrangement may be considered similar to the arrangement shown in FIGS. 9 and/or 10, 11 and 12. More particularly, the combination of control module 1308 and HDS system 1310 will control the flow 1302a entering HDS system 1310, such that proper operations of the HDS system 1310 are undertaken in consideration of the data obtained from the test module 1306. In addition to controlling the variables such as discussed in connection with FIG. 9, control module 1308 will control a variable output splitter mechanism 1320 shown in a exploded image. More particularly, a flow diverter 1322 is positioned at the output 1324 of HDS system 1310 and is configured to move (e.g., one manner it is configured to have a pivoting capability, another arrangement is to control operation of pressure control valves of FIG. 9) such that as water is flowing in the out direction 1326, the flow diverter 1322 is controlled to split the water between output channels 1324a, 1324b in a ratio dependent on values determined by the operation of control module 1308.

The output of the water stream with removed biological contaminants is shown as stream 1302b. The highly concentrated waste stream having biological contaminants is shown as stream 1328 and is provided to a waste container 1330. The waste container may represent any arrangement used to dispose of or further clean or eliminate biological components in waste stream 1328.

Similar to that discussed in the first set of operations, water flow 1302b is partially diverted by diverter path 1340a to a test module 1342, where the results of the test module 1342 are provided to a control module 1344. Using the information and data on the flow, biological contaminant proportion, size, etc., adjustments are made to the HDS system 1346. As previously occurred, the flow of diverter path 1340a that was not employed is returned via return path 1340b to main stream 1302b. Again, similar to the previous processes, the further processed algae water is output from HDS system 1346 as stream 1302c, and waste stream 1348 is provided to waste container 1350.

The system of FIG. 13 illustrates the capability of a continuous processing of algae water. It is further appreciated that, while this is in a serial connection, multiple connections may be provided to process a quantity of fluid being cleaned. Therefore, for example, instead of a single line of fluid going into HDS system 1346, multiple inputs (e.g., 1360a, . . . , 1360n) may be provided, and the HDS system 1346 may be larger than the system 1310 to handle the additional input. It is noted the input lines 1360a, . . . , 1360n are shown distant from the HDS system 1346. However, this is shown for clarity of FIG. 13, and in operation, input lines 1360a to 1360n would be in operational contact with HDS system 1346. Further boxes 1370a to 1370n are understood to represent the entirety of the embodiments of the system generating the output flow at line 1302b, including but by no way limited to components such as the test module, control module, HDS system, as well as the associated lines and flow paths.

The testing taking place in the test modules 1306 and 1342 can be accomplished in-line (i.e., concurrently) with the biological contaminants removal operations. Alternatively, such testing may be undertaken prior to such operations.

While FIG. 13 includes diversion paths 1304a and 1340a, and return paths 1304b and 1340b, alternative arrangements can be employed. For example instead of diverting flow to the testing modules 1308 and 1344, the system 1300 (and other embodiments) can employ sensors in any or all of the flow paths 1302a, 1302b, and 1302c (the sensors can be those such as described in connection with FIG. 9 for example) and the data collected from these sensors would be provided to any or all of control modules 1308 and 1342 to control operation of the HDS systems 1310 and 1346.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A method for removing biological contaminants from an algal crop, the method comprising:
   providing a flow of an algal crop containing biological contaminants to a hydrodynamic separator (HDS) system;
   controlling the flow by a control module, wherein the biological contaminants are concentrated into a first portion of the flow of the algal crop within the HDS system, based on a size of the biological contaminants, wherein the first portion contains a majority of the biological contaminants in the flow of the algal crop and a second portion contains a majority of algae in the flow of the algal crop;
   splitting the flow of the algal crop by use of a bi-furcated output of the HDS system, wherein the splitting is between the first portion containing the majority of the biological contaminants in the flow of the algal crop and the second portion which contains the majority of the algae of the algal crop; and
   outputting the first portion of the flow of the algal crop containing the majority of the biological contaminants from a first output of the bi-furcated output, and outputting the second portion of the flow of the algal crop containing the majority of the algae of the algal crop.

2. The method according to claim 1 wherein the first portion further includes an amount of the algal crop, wherein the amount of the algal crop in the first portion is proportional to a flow ratio between the first portion and the second portion.

3. The method according to claim 1 wherein a flow split ratio between the first portion and the second portion is 50:50, wherein the second value, 50, of the flow split ratio contains larger particles which are the biological contaminants.

4. The method according to claim 1 wherein a flow split ratio between the first portion and the second portion is 70:30, wherein the second value, 30 of the flow split ratio contains larger particles which are the biological contaminants.

5. The method according to claim 1 wherein a flow split ratio is variable based on geometry of the HDS system and the split design.

6. The method according to claim 1 wherein the HDS system is designed to have a particle cut-off size of between 10 to 100 μm, an operating pressure of 1 to 40 psi (pounds per square inch), a curved flow path of between 180 and 360 degrees, a flow rate per channel of 0.1 to 2.0 lpm (liters per minute), a mass capture of the biological contaminants of between 80% to 95%, and a flow split ratio of between 50:50 to 90:10 wherein the second value, between 50 and 10, of the flow split ratio contains larger particles which are the biological contaminants.

7. The method according to claim 1, wherein the operation of the HDS system is intermittent.

8. The method according to claim 1 wherein the operation of the HDS system is continuous.

9. The method according to claim 1 further including:
inline testing of the flow carrying the algal crop for biological contaminants, wherein the flow includes water carrying the algal crop;
determining fluid flow characteristics
providing the test results to a control module of the HDS system; and
adjusting the operational characteristics of the HDS system by the control module based on the test results.

10. The method according to claim 1 wherein the first portion further includes an amount of the algal crop, wherein the amount of the algal crop in the first portion is proportional to a flow split ratio between the first portion and the second portion and the flow split ratio as adjustable by control of the HDS system.

11. The method accruing to claim 1 wherein the biological contaminants include at least one of paramecium between 50 μm and 330 μm in size, amoeba between 250 μm and 750 μm in size, and rotifer between 100 μm and 500 μm in size.

12. The method according to claim 1 wherein a cut-off size is 20 μm, with a flow split ratio of 70:30.

13. The method according to claim 12 wherein 90% of biological contaminants are removed from the flow of the algal crop.

14. The method according to claim 1 wherein testing includes testing for at least one of a type of biological contaminant, size of the biological contaminant, and concentration of the biological contaminant in the water.

15. The method according to claim 1 wherein testing includes testing for at least one of, testing for discoloration, testing for unusual odor, testing for biofouling, testing for foam production, and testing for auto-flocculation.

16. The method of claim 1 wherein the HDS system includes a curved channel design.

17. A system for removing biological contaminants from an algal crop, the system comprising:
a flow of an algal crop containing biological contaminants, provided to a hydronamic separator HDS system;
a control module to control the flow, wherein the biological contaminants are concentrated into a first portion of the flow of the algal crop within the HDS system, based on a size of the biological contaminants, wherein the first portion contains a majority of the biological contaminants in the flow of the algal crop and a second portion contains a majority of algae in the flow of the algal crop;
a bi-furcated output of the HDS system to split the flow of the algal crop, wherein the split is between the first portion containing the majority of the biological contaminants in the flow of the algal crop and the second portion which contains the majority of the algae of the algal crop; and
a first output of the bi-furcated output to output the first portion of the flow of the algal crop containing the majority of the biological contaminants, and a second output of the bi-furcated output to output the second portion of the flow of the algal crop containing the majority of the algae of the algal crop.

18. The system according to claim 17 wherein the first portion further includes an amount of the algal crop, wherein the amount of the algal crop in the first portion is proportional to a flow split ratio between the first portion and the second portion.

19. The system according to claim 17, wherein a flow split ratio is variable based on geometry of the HDS system and the split design.

20. The system according to claim 17, wherein the HDS system includes a curved channel design.

* * * * *